(12) United States Patent
Djordjevic

(10) Patent No.: US 8,545,094 B2
(45) Date of Patent: Oct. 1, 2013

(54) DETECTING A MINERAL WITHIN A MATERIAL

(75) Inventor: Nenad Djordjevic, Queensland (AU)

(73) Assignee: Technologies Resource Pty Limited, Melbourne (AU)

( * ) Notice: Subject to any disclaimer, the term of this patent is extended or adjusted under 35 U.S.C. 154(b) by 0 days.

(21) Appl. No.: 13/202,935

(22) PCT Filed: Feb. 23, 2010

(86) PCT No.: PCT/AU2010/000205
§ 371 (c)(1),
(2), (4) Date: Apr. 5, 2012

(87) PCT Pub. No.: WO2010/094087
PCT Pub. Date: Aug. 26, 2010

(65) Prior Publication Data
US 2012/0181221 A1   Jul. 19, 2012

(30) Foreign Application Priority Data
Feb. 23, 2009   (AU) ............................. 2009900781

(51) Int. Cl.
*G01J 5/00*   (2006.01)
(52) U.S. Cl.
USPC ................. 374/122; 374/4; 374/45; 209/539; 209/576

(58) Field of Classification Search
USPC .......................... 209/539, 576; 374/122, 4, 45
See application file for complete search history.

(56) References Cited

U.S. PATENT DOCUMENTS

| | | | | |
|---|---|---|---|---|
| 4,212,397 A | * | 7/1980 | Bockelmann | 378/47 |
| 5,170,666 A | * | 12/1992 | Larsen | 73/571 |
| 5,209,355 A | * | 5/1993 | Mindermann | 209/3.1 |
| 8,100,581 B2 | * | 1/2012 | Djordjevic | 374/122 |
| 8,233,667 B2 | * | 7/2012 | Helgason et al. | 382/109 |
| 8,446,156 B2 | * | 5/2013 | Morrison | 324/637 |
| 2009/0013822 A1 | | 1/2009 | Shaw | |
| 2009/0314086 A1 | | 12/2009 | Djordjevic | |

FOREIGN PATENT DOCUMENTS

| WO | WO 2006/034553 A1 | 4/2006 |
|---|---|---|
| WO | WO 2007/051225 A1 | 5/2007 |
| WO | WO 2008/017107 A1 | 2/2008 |

OTHER PUBLICATIONS

International Search Report from the Australian Patent Office for International Application No. PCT/AU2010/000205, mailed May 5, 2010.

* cited by examiner

*Primary Examiner* — Kaitlin Joerger
(74) *Attorney, Agent, or Firm* — Banner & Witcoff, Ltd.

(57) ABSTRACT

The invention exposes rock fragments of a material to electromagnetic radiation, such as microwave radiation, and detects the thermal response of the material of the rock fragments during or immediately after exposure to detect a mineral within the material.

37 Claims, 17 Drawing Sheets

DETECTING A MINERAL WITHIN A MATERIAL

CROSS-REFERENCE TO RELATED APPLICATIONS

This application is a national phase application of International Application No. PCT/AU2010/000205, filed Feb. 23, 2010, and claims the priority of Australian Patent Application No. 2009900781, filed Feb. 23, 2009.

The invention relates to a method determining the presence or absence of a mineral within a material.

By way of example, the invention relates to method determining the presence or absence of a copper-containing mineral within a material in the form of a copper-containing ore. In this application, the invention is concerned particularly, although not exclusively, with making it possible to discriminate between chalcopyrite and less valuable minerals of pyrite and arsenopyrite. It is noted that the invention is not limited to copper-containing minerals.

The invention also relates to a method of sorting rock fragments, such as ore fragments, of a material based on the above method.

The invention also relates to an apparatus for determining the presence of a mineral within a material.

More particularly, the invention relates to a method and an apparatus that are based on exposing rock fragments of a material to electromagnetic radiation, such as microwave radiation, and detecting the thermal response of the material of the rock fragments to detect a mineral within the material.

The invention has particular but not exclusive application to assessing mineral content and/or distribution within and on the surface of rock fragments, of a material and for downstream sorting of target minerals from other components of the material. For illustrative purposes, particular reference will be made to this application. However, it is to be understood that this invention could be used in other applications, such as assessing mineral content and/or distribution within rock bodies in situ, in soils or sands, in mining, in other geological contexts and in research.

SUMMARY OF THE INVENTION

The invention exposes rock fragments of a material to electromagnetic radiation, such as microwave radiation, and detects the thermal response of the material of the rock fragments during or immediately after exposure to detect a mineral within the material.

More particularly, the invention provides a method of detecting a mineral in a target material comprising:
 (a) applying electromagnetic radiation to the material;
 (b) detecting thermal radiation emitted from the material during or immediately after exposure of the material to the radiation; and
 (c) analysing the thermal radiation to determine the presence of the mineral in the material.

In effect, the invention is based on the detection of localised hot spots of a material, for example on the surface of rocks or rock fragments of the material. The invention does not require the detection of an increase of average temperature of entire rocks or rock fragments of a material by say 2-3° C. Consequently, the total volume of material analysed may represent only 5% of the total rock volume. An increase of temperature that can be used as a basis for analysis need only be 2-3° C. As a consequence, the energy requirements for the method may be 1/10 to 1/20 of the energy requirements for a method based on heating entire rock fragments. The economic benefit of sorting ore increases with increasing size of rocks or rock fragments. For example, for many copper ore types, due to the random distribution of copper-containing minerals, the invention provides an opportunity for determining the presence of copper minerals in the rocks or rock fragments by surface analysis—based on the number of hot spots being representative of the grade of copper in the rocks or rock fragments. In addition, it has been found that detection of the thermal response of a material during or immediately after exposure to electromagnetic radiation allows sharp, distinct images of the mineral distribution within the material to be produced. These images facilitate identification of the type of minerals present. It has been found in work on copper-containing ores containing chalcopyrite and pyrite that the method exploits differential heating rates of certain minerals within a material to the extent that it is possible to discriminate between chalcopyrite and pyrite minerals. This is a significant finding. The work found that an image could be captured showing the location of the heated minerals within a material before the heat dissipated to other, relatively cool parts of the material that did not absorb the applied microwave radiation as quickly as the minerals or before the heat was lost to the surroundings. Dissipation of the heat is undesirable because it results in a loss of diagnostic ability for minerals within the material.

The method may comprise detecting thermal radiation emitted from the material while the material remains in an electromagnetic containment zone.

The method may comprise detecting thermal radiation emitted from the material during exposure of the material to radiation.

The method may comprise detecting thermal radiation emitted from the material within 2.0 seconds of exposure of the material to radiation.

The method may comprise detecting thermal radiation emitted from the material within 1.0 seconds of exposure of the material to radiation.

The method may comprise detecting thermal radiation emitted from the material within 0.5 seconds of exposure of the material to radiation.

Step (a) of the method may comprise selecting the radiation and the exposure conditions such as the exposure time to heat the target mineral to a temperature which is significantly higher (for example, at least 5° C., typically at least 20° C., and more typically in a range of 5-50° C.) than the temperature of other components of the material.

The invention also provides a method of detecting a mineral in a material comprising:
 (a) applying electromagnetic radiation to the material;
 (b) detecting thermal radiation emitted from the material during or immediately after exposure of the material to the radiation;
 (c) determining the rate of heating of the material, or a part thereof; and
 (d) analysing the rate of heating to determine the presence of the mineral in the material.

The electromagnetic radiation may be low energy radiation, such as energy densities less than 1000 MW/m$^3$, typically less than 100 MW/m$^3$. In the case of electromagnetic radiation in the form of microwave radiation, the microwave power may be less than 900 W, typically less than 600 W.

The low energy electromagnetic radiation may be applied to the material as it enters an electromagnetic radiation exposure zone and the rate of heating of the material, or part thereof, may be measured during or immediately after exposure to facilitate the analysis.

The term "mineral" is understood herein in a broad sense. The term includes non-organic minerals, such as azurite, bornite, chalcocite, chalcopyrite, covellite, cuprite, galena, magnetite, malachite, hematite, pyrite, pyrhotite, sphaleraite, tennantite, tetrahedrite, and uraninite. The term includes organic geological compounds, such as heavy oil, light oil, bitumen, etc.

The term "material" is understood herein in a broad sense. The term includes rocks, rock fragments, soils, sands and other geological materials whether in situ or not.

The electromagnetic radiation may be any suitable electromagnetic energy.

For example, electromagnetic radiation may be microwave energy.

By way of further example, the electromagnetic radiation may be radio frequency radiation.

The electromagnetic radiation may be continuous or pulsed.

The pulse duration and/or the frequency of electromagnetic radiation may be selected such that:
(a) the heating of surface moisture and/or absorbed moisture within the material is minimised;
(b) the thermal differential between the electromagnetic radiation absorbing target mineral and other components in the material, such as other minerals and gangue material is maximised;
(c) the heating of gangue material is minimised; and
(d) the target mineral in the material is otherwise suitably affected by the electromagnetic radiation.

The duration of the pulses may be up to 1 second, preferably from 0.01-1 seconds, and more preferably from 0.1 to 1 seconds. Generally the duration of the pulses is 0.1-0.3 seconds. The time period between pulses may be any suitable time period.

The electromagnetic radiation may be applied at a low power density to avoid the possibility of forming microfractures in the rock fragments. The amount of electromagnetic radiation that will induce fracture will vary from case to case.

In situations where the electromagnetic radiation is microwave radiation, the pulsed microwave radiation may be applied at a power density below 1000 $MW/m^3$, more preferably in a range of 1-100 $MW/m^3$.

In situations where the electromagnetic radiation is microwave radiation, the frequency may be in a range of 400-5800 MHz, more preferably in the range of 900-3500 MHz, even more preferably 915-2450 MHz, and most preferably in the range of 915-950 MHz.

The method of detecting the thermal radiation emitted from the material may be any suitable method. For example, a thermal imager such as an infra red camera may be used. Detection of the thermal radiation may be performed within the spectral range of infra red radiation within which the target mineral is characterised as having its highest differential emissivity relative to the host (background) material.

The step of determining the rate of heating of the material may comprise recording the temperature change of the material at regular time intervals.

In addition, the method may comprise correlating the measured rate of heating to a pre-determined rate of heating for a particular mineral. Advantageously, this will allow identification of the target mineral present in the material.

The method of the invention may be applicable for in situ analysis of the material, for example for determining mineral content in a body or ore in situ. Generally, the method is applicable to rock fragments or other material samples, such as sand samples or soil samples that are removed from their in situ site.

The material may be fed into an electromagnetic radiation exposure zone in a single feed channel. Alternatively, to increase throughput the material may be fed into the zone in a plurality of separate feed channels. In either case, where the material includes rocks or rock fragments, the rocks or rock fragments may be fed into the zone single file in the one or more channels.

The invention also provides a method of sorting a feed stream of material into at least two streams including:
(a) determining the presence of a target mineral in the feed stream of material using the method as described above; and
(b) separating the feed stream of material into the at least two streams based on that determination.

The feed stream may be separated into at least a waste stream and a product stream.

The feed stream may be separated into a waste stream and a plurality of product streams based on mineral grade of the material.

Separation of the feed stream into at least two separate streams may be by any suitable means. For example, the feed stream may be separated into the at least two streams by a high pressure air blower.

The invention provides an apparatus for determining the presence of a target mineral within a material including:
(a) an electromagnetic radiation exposure zone including an electromagnetic radiation emitter adapted to emit radiation into the exposure zone;
(b) a detector for thermal radiation emitted from the material during the application of electromagnetic radiation to the material; and
(c) an analyser for interpreting the thermal radiation detected by the detector or for determining the rate of heating of the material, or portion thereof, based on the thermal radiation detected by the detector, and for thereby determining the presence of the mineral within the material.

The electromagnetic radiation emitter may be adapted to emit pulsed radiation into the exposure zone.

The exposure zone may be arranged such that the material being analysed passes vertically through the zone. In that way, the material being analysed, for example in the form of rocks or rock fragments, may simply fall under gravity through the zone. Alternatively, the material may pass horizontally through the zone along a conveyer belt. In that case, multiple particles of the material may be analysed simultaneously.

In order to facilitate processing a large volume of material in a uniform and continuous manner, in situations where the electromagnetic radiation is in the form of microwave radiation, the emitter may be in the form of a multimode microwave cavity, preferably equipped with a suitable stirrer.

The detector may be a thermal imager such as an infra-red imager.

The apparatus may comprise two or more than two thermal imagers.

The thermal imager or imagers may be positioned about the microwave cavity to simultaneously detect radiation emitted from the material, generally over a period of time, as rocks or rock fragments of the material pass through the microwave exposure zone. The location of the imager(s) about the cavity is not particularly limited. For example, when the exposure zone is arranged such that the material being analysed is passed vertically therethrough, the imager(s) may be located near the top, middle or bottom of the zone. Preferably, the imager(s) are located at or near the middle of the exposure zone.

The thermal imager(s) may be located within 50 cm of the rock or rock fragments passing through the exposure zone.

The imager(s) may be located within 30 cm of the rocks or rock fragments passing through the exposure zone.

In situations where the speed of the material through the microwave irradiation zone is up to several metres per second, it is important that the material residence time within the microwave irradiation zone be sufficiently long to induce the required amount of heating of the target mineral to allow for identification.

The analyser may be a computer that comprises image processing software. Advantageously, this will enable continuous and automated processing and analysis of a feed of material.

The apparatus may comprise a visible light camera or other means for gauging the size of material passing through the exposure zone. This may particularly be the case where the material includes rock fragments.

The apparatus may be configured to facilitate sorting of material passing through the exposure zone.

The apparatus may comprise a sorter for sorting the material into at least two streams.

The material may be fed to the exposure zone by any suitable means.

DETAILED DESCRIPTION OF THE INVENTION

The invention is described further by way of example with reference to the accompanying drawings, of which:

As is evident from the above description of the drawings, the following description is in the context of the use of electromagnetic radiation in the form of microwave radiation. It is noted that the invention is not confined to the use of microwave radiation and extends to the use of any suitable electromagnetic radiation.

Figure 1:
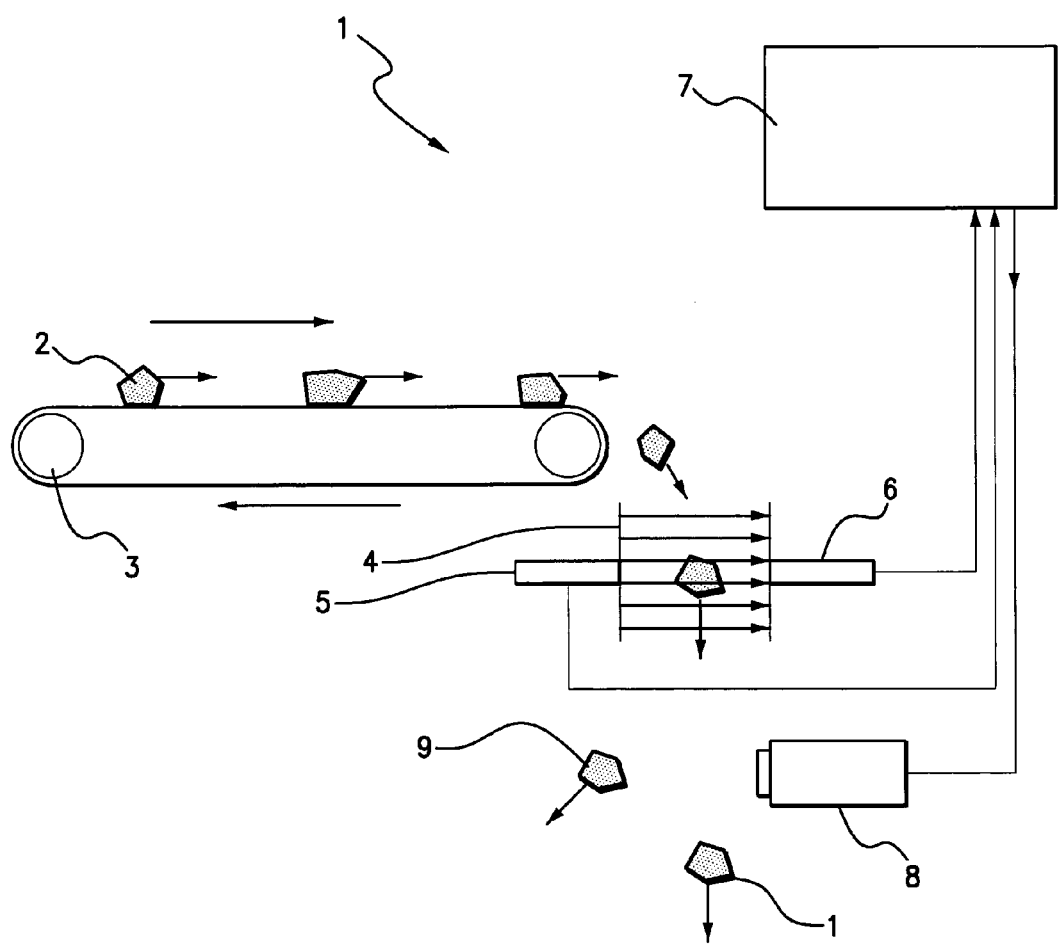
FIG. 1 illustrates an apparatus according to one embodiment of the invention.

In the embodiment of the apparatus shown in FIG. 1, rock fragments (2) are transported by a conveyor belt (3) that terminates above a microwave radiation exposure zone in the form of a multimode or single mode microwave cavity (4). The rock fragments (2) fall vertically through the microwave cavity (4). Although the rock fragments (2) may pass through the cavity (4) in any direction, falling vertically is advantageous as it increases the likelihood of uniform exposure of rock fragments to radiation as the fragments tumble through the cavity (4).

The rock fragments pass through the cavity (4) individually so that each fragment (2) can be analyzed individually.

Within the microwave cavity (4) the rock fragments (2) are exposed to pulsed microwave radiation of a selected microwave frequency and microwave intensity depending on the mineral or grade of interest. The pulsed microwave radiation may be applied at a power density below that which is required to induce micro-fractures in the rock fragments as previously described. Generally, the pulsed microwave radiation will be applied at a power density within a microwave absorbing phase of below 100 MW/m$^3$.

While passing through the microwave cavity (4), radiation emitted from the rock fragments (2) is detected by high resolution, high speed infrared imagers (5) and (6) which capture thermal images of the rock fragments (2). While one thermal imager is sufficient, two or more thermal imagers (5, 6) may be used for full coverage of the rock particle surface. As depicted in FIG. 1, the thermal imagers (5, 6) are located at or near the middle of the cavity (4). However, the thermal imagers (5, 6) may be located at other locations of the cavity such as closer to the conveyor belt (3) or an air blower (8). The thermal imagers (5, 6) need not be level with each other. Images collected by the thermal imagers (5, 6) are processed using a computer (7) equipped with image processing software. The thermal imagers (5, 6) may also be used for determination of the size of the rock fragments (2).

Alternatively, or in combination, one or more visible light cameras (not shown) may capture visible light images to allow determination of fragment size. From the number of detected hot spots (pixels), temperature, pattern of their distribution and their cumulative area, relative to the size of the fragment, an estimation of the grade of observed rock fragments can be made. This estimation may be supported and/or more mineral content may be quantified by comparison of the data with previously established relationships between microwave induced thermal properties of specifically graded and sized rock fragments.

Based on the content analysis individual rock fragments (2) may then be separated using a separator in the form of a high pressure air blower (8). Any appropriate conventional device may, however, be used. The air blower (8) separates the individual rock fragments (2) based on information sent by the computer (7). The individual rock fragments (2) may be separated on the basis of, for example, estimated grade, quantified mineral content and/or location of mineral pockets within or on the surface of the rock fragments (2).

In the apparatus depicted in FIG. 1, the high pressure air blower (8) may receive a signal from the computer (7) to release air at the moment a rock fragment (9) containing a high mineral content (such as chalcopyrite or bornite) passes it such that that fragment (9) is directed to a specific collector. Low grade or gangue particles (10) (for example, pyrite) may be allowed to continue their free fall into a separate collector. In this particular embodiment for ease of understanding the fragments have only been divided into two groups. However, it should be realized that this apparatus and method can be configured to separate the rock fragments (2) across a scale of mineral content. In such a configuration, the high pressure air blower (8) may blow air 15 at varying forces and/or directions, or multiple blowers could be used, for example for each fragment grade, to direct specific fragments to specific collectors dependent upon the level of mineral content or distribution pattern of the mineral within the fragments. Alternatively, or in combination, separate conveyer belts may be used to direct the rock fragments to separate collectors.

The use of pulsed low power microwave radiation enables the mineral of the rock fragments to heat quickly without distributing the surrounding rock. The chance of surrounding rock being heated and therefore adversely impacting on detection is increased if imaging is conducted after a time period of 5 seconds after exposure to microwave radiation. Detection of the thermal radiation emitted from a rock fragment during exposure to microwave radiation or immediately after exposure, i.e. within 4 seconds, results in a thermal image that is well defined and allows the mineral to be pinpointed within the rock fragment. One advantage of this is that an accurate quantification of mineral content can be achieved. Another advantage is that rock fragments may be sorted across a scale of mineral content rather than a rudimentary analysis of high level or low/no mineral content.

In order to illustrate the invention in further detail, reference is now made to FIGS. 2 through 20. The differential heating (and simultaneous imaging thereof) of various rock fragments is clearly illustrated in the Figures and graphs which are described briefly below.

Figure 2:
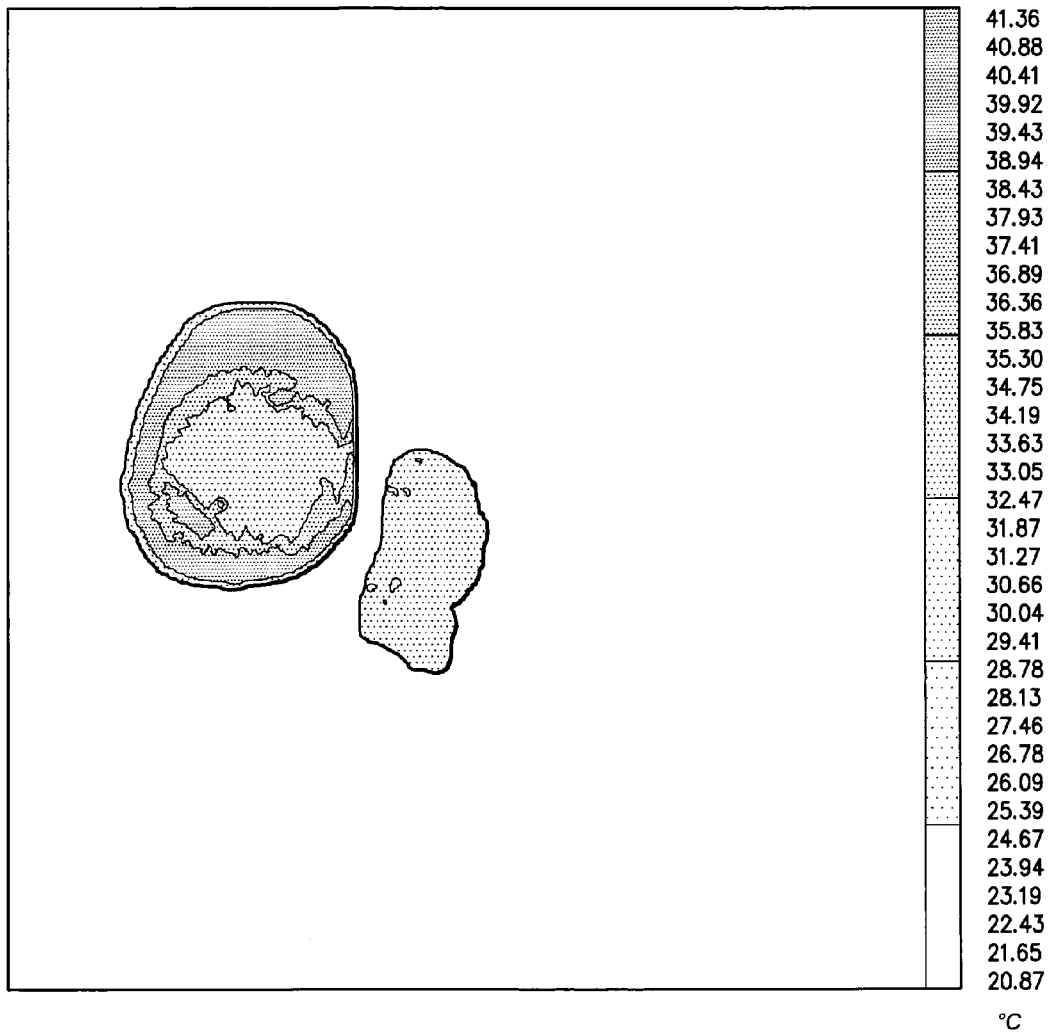
FIG. 2 is an IR image of a chalcopyrite mineral grain (left) and a pyrite mineral grain (right) after brief exposure to microwave irradiation.

FIG. 2 illustrates a chalcopyrite mineral grain on the left and a pyrite mineral grain 10 on the right after application of low power microwave radiation (600 W). The chalcopyrite mineral grain clearly has a higher temperature around its periphery than the pyrite mineral grain which has undergone comparatively less and more uniform heating. The central area of the chalcopyrite grain has approximately the same temperature as the pyrite grain.

Figure 3:
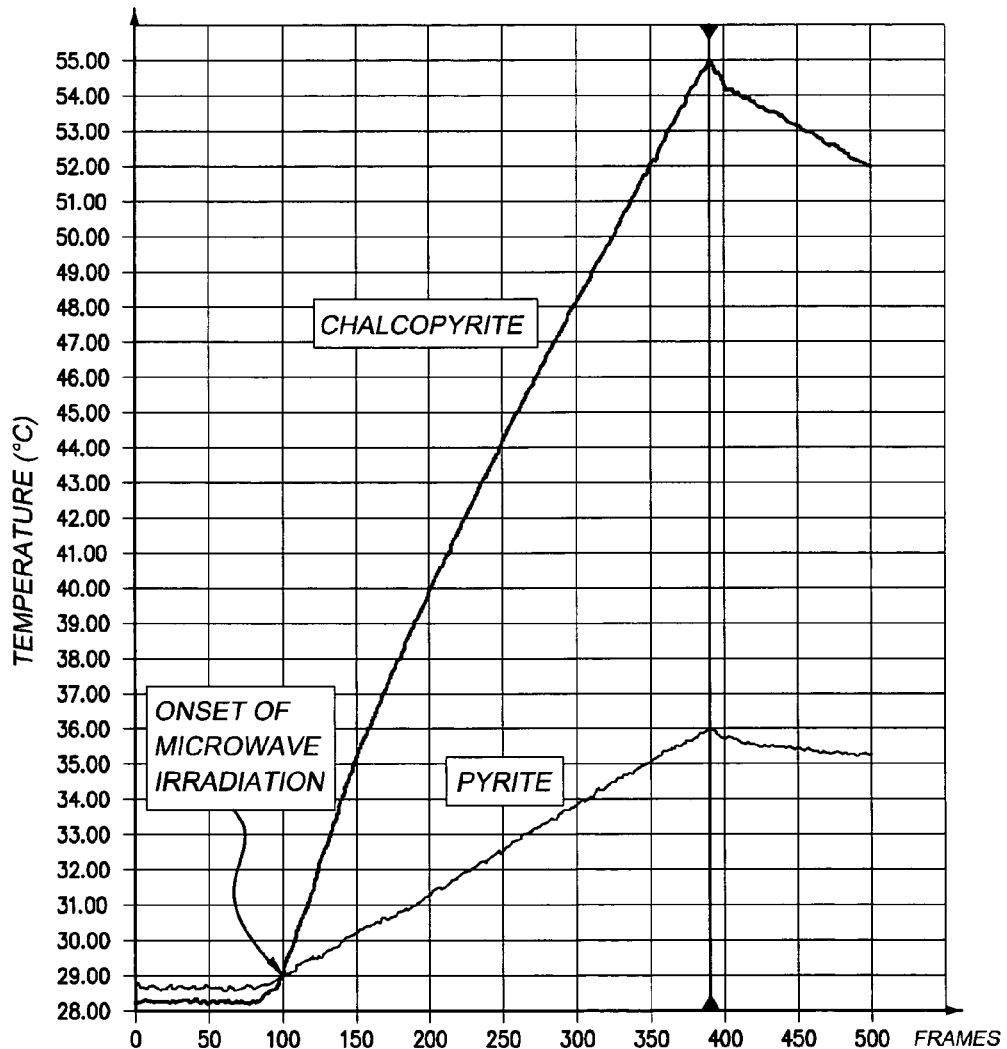
FIG. 3 is a graph showing the change in temperature of the mineral grains in FIG. 2 with time as they are subjected to microwave radiation.

The graph in FIG. 3 quantifies the change in temperature of the mineral grains in FIG. 2 with time as they are heated with microwave radiation. Prior to application of the microwave radiation, the grains are approximately the same temperature. Upon application of the microwaves the grains begin to rise in temperature. The rate of temperature rise of the chalcopyrite grain is much higher than the pyrite grain. In fact, the maximum temperature of the chalcopyrite grain (55° C.) is approximately one and a half times that of the pyrite grain (36° C.) after the same length of time. At this point the microwave radiation is no longer applied to the grains and their temperatures begin to lower. Thus, microwave irradiation is an effective means for distinguishing chalcopyrite and pyrite samples.

Figure 4:
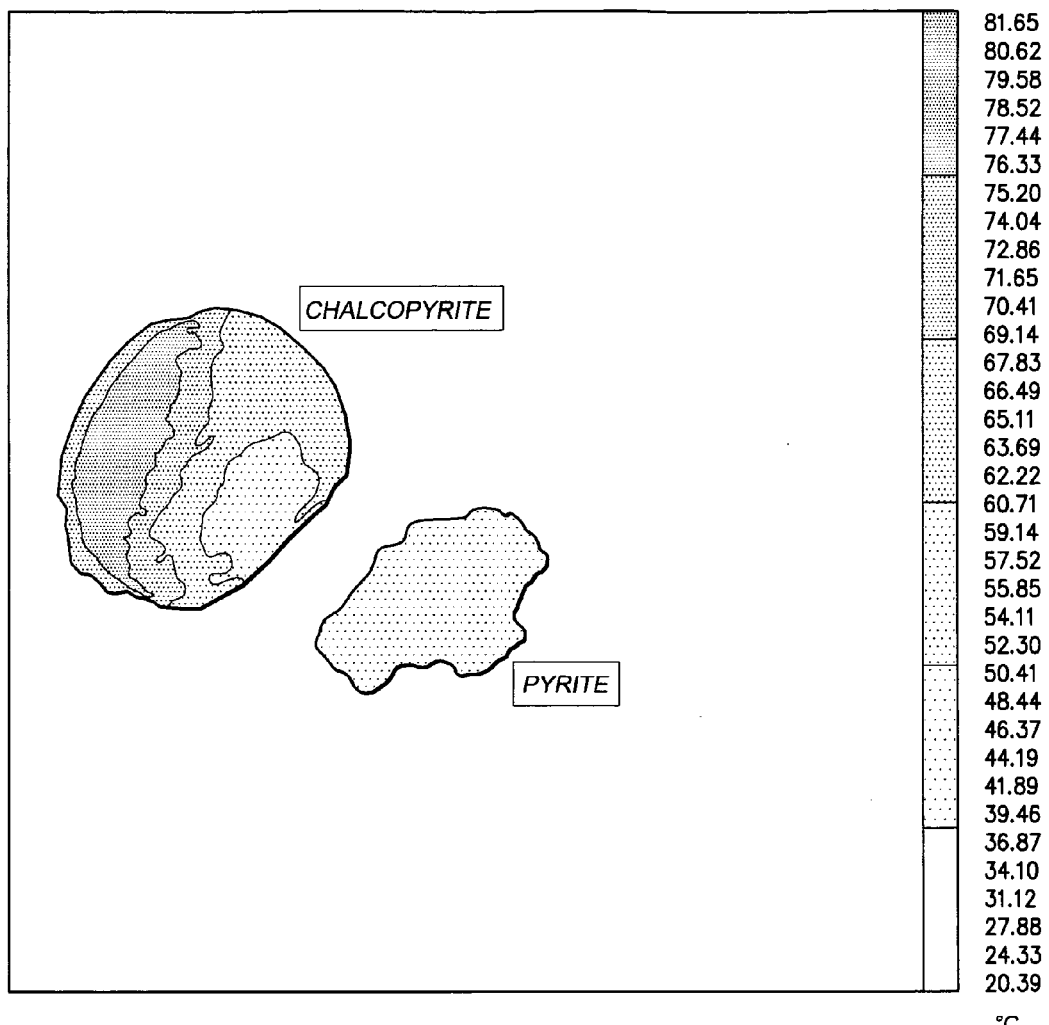
FIG. 4 is an IR image of a chalcopyrite crystal (left) and a pyrite crystal (right) after exposure to pulsed microwave irradiation.

FIG. 4 is an IR image of a chalcopyrite crystal on the left and a pyrite crystal on the right after exposure to pulsed microwave radiation. Clearly, the chalcopyrite crystal has undergone significant heating with certain regions of the crystal having a higher temperature than other regions. In contrast, the pyrite crystal has a relatively uniform and overall lower temperature. The two samples are easily distinguished from each other.

Figure 5:
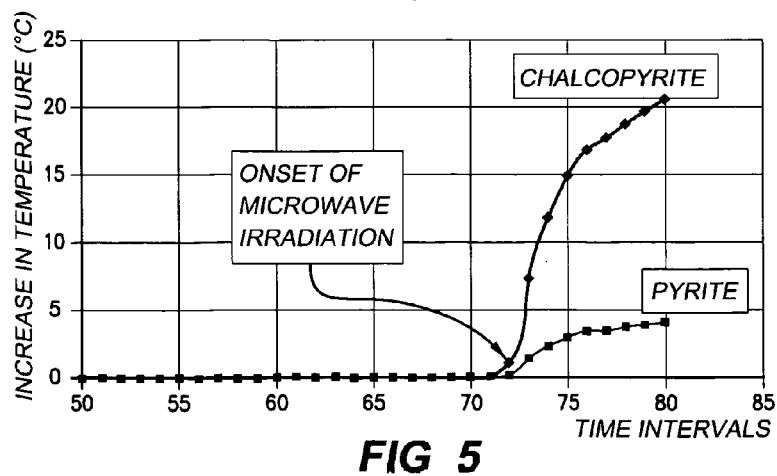
FIG. 5 is a graph illustrating the change in temperature of the chalcopyrite and pyrite crystals in FIG. 4 with time as they are subjected to pulsed microwave radiation.

FIG. 5 is a graph illustrating the change in temperature of the chalcopyrite and pyrite crystals in FIG. 4 with time. Prior to application of pulsed microwave radiation, the there is no temperature difference between the crystals. Once microwave radiation is applied the temperature of both crystals begins to rise. However, the rate of temperature increase of the chalcopyrite crystal is much faster than the pyrite crystal over the same period of time.

Figure 6:
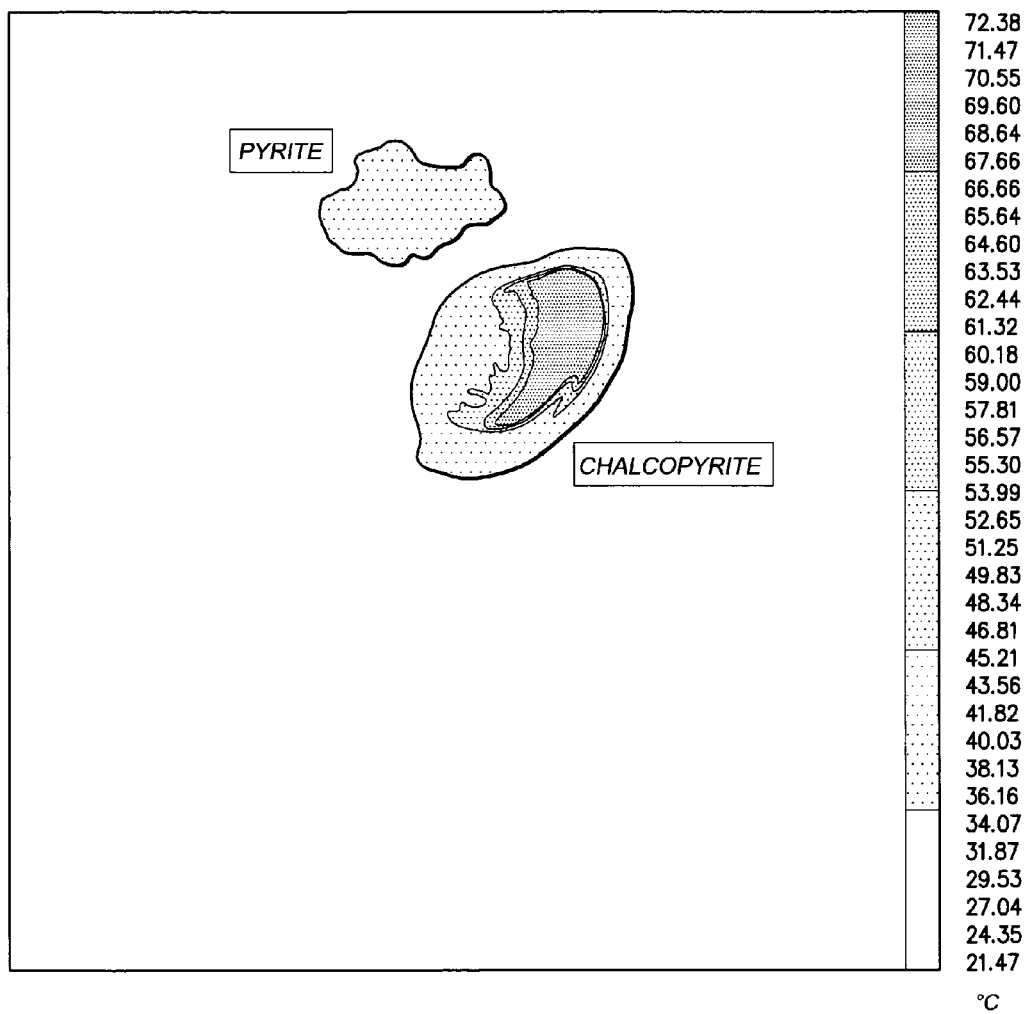
FIG. 6 is another IR image of a chalcopyrite mineral grain (bottom right) and a pyrite mineral grain (top) after brief exposure to microwave irradiation.
Figure 7:
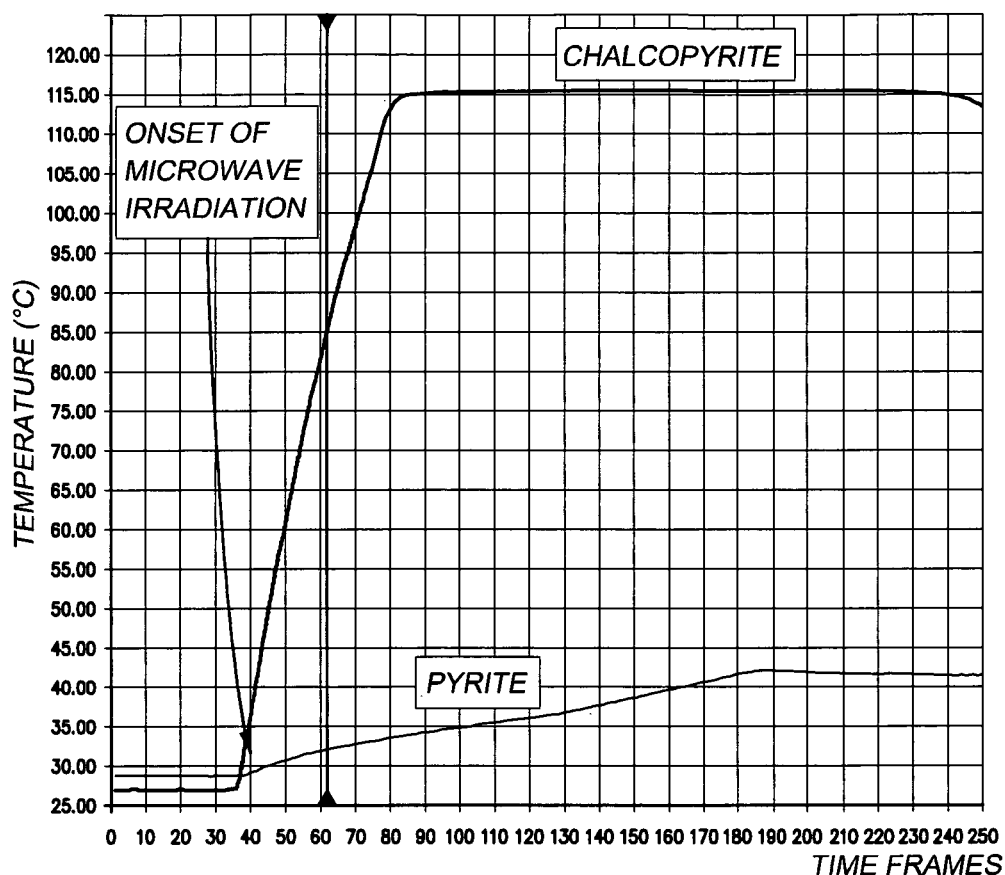
FIG. 7 is a graph showing the change in temperature of the chalcopyrite and pyrite grains in FIG. 6 with time as they are subjected to microwave irradiation.

FIG. 6 is another IR image of a chalcopyrite mineral grain (bottom right) and a pyrite mineral grain (top left) after one second exposure to microwave irradiation. Again, the temperature differential between the grains is obvious as well as within the chalcopyrite grain per se. The graph in FIG. 7 shows the relationship between the temperature of the chalcopyrite and pyrite grains in FIG. 6 with time during the heating process. After one second of microwave irradiation the heating rate of the chalcopyrite grain is 54.3° C./second and the pyrite grain is 3.5° C./second.

Figure 8:
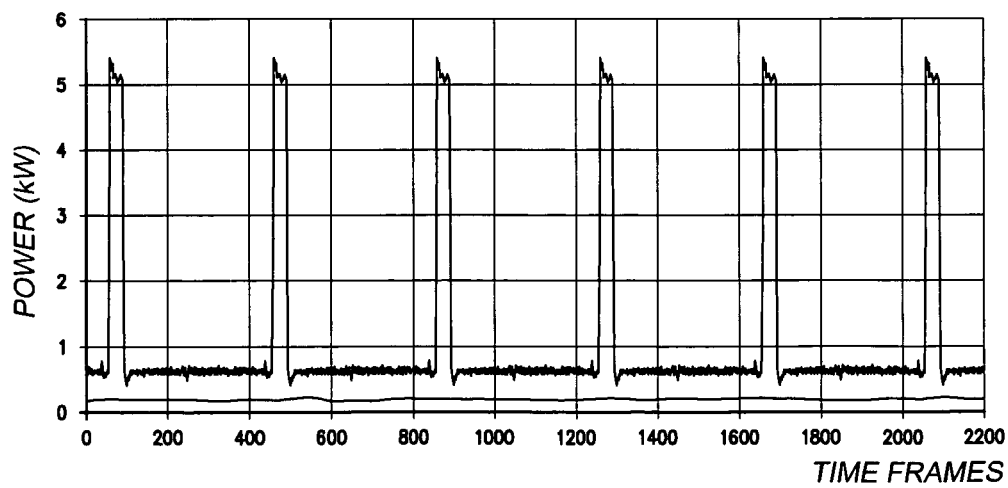
FIG. 8 is a graph depicting the variation in forward and reflected power of microwaves with time as applied during microwave pulsing.

FIG. 8 is a graph depicting the variation in forward and reflected power of microwaves with time as applied during microwave pulsing. As will be evident, the duration of the pulsed radiation is much shorter than the time interval between each pulse. This pattern avoids excessive heating of the material under investigation thereby facilitating production of high quality images.

Figure 9:
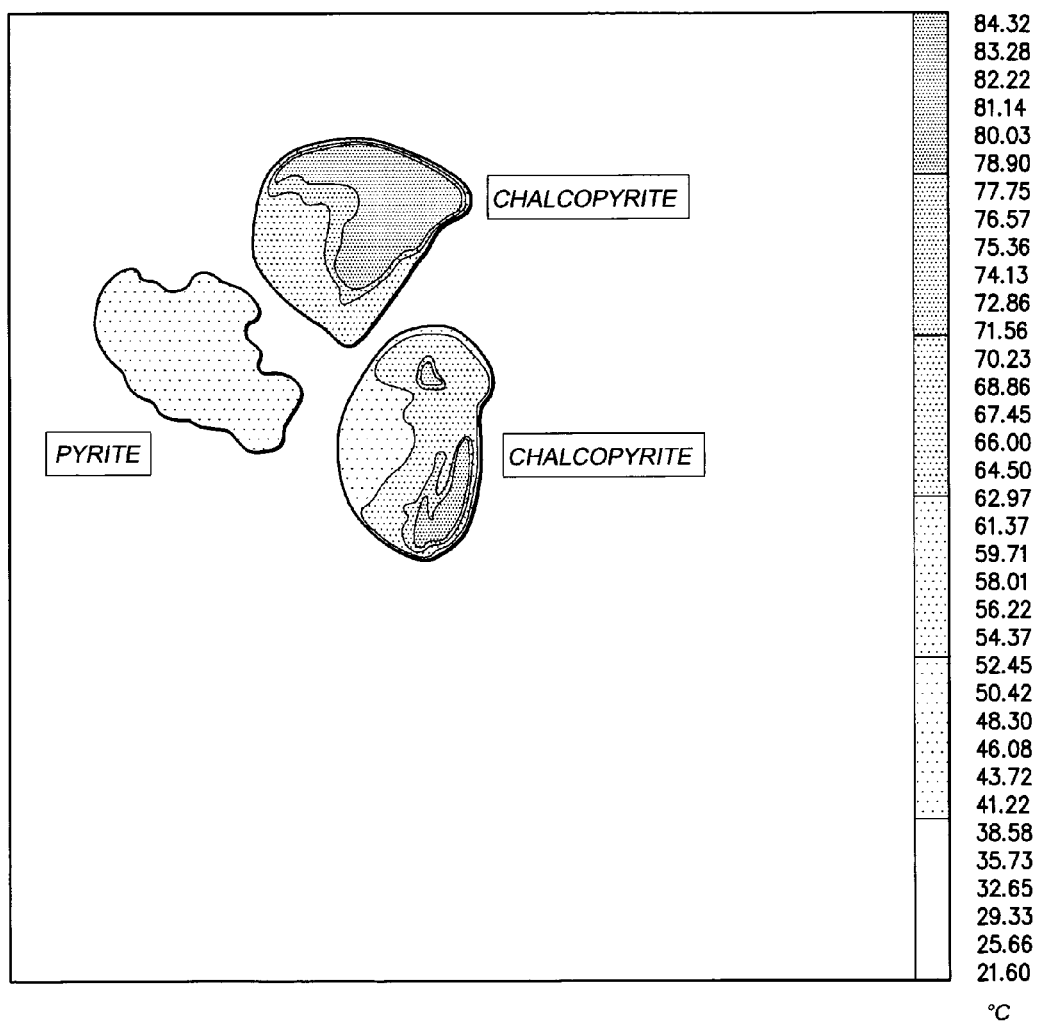
FIG. 9 is an IR image of two chalcopyrite grains (right) and a pyrite grain (left) after exposure to microwave irradiation.
Figure 10:
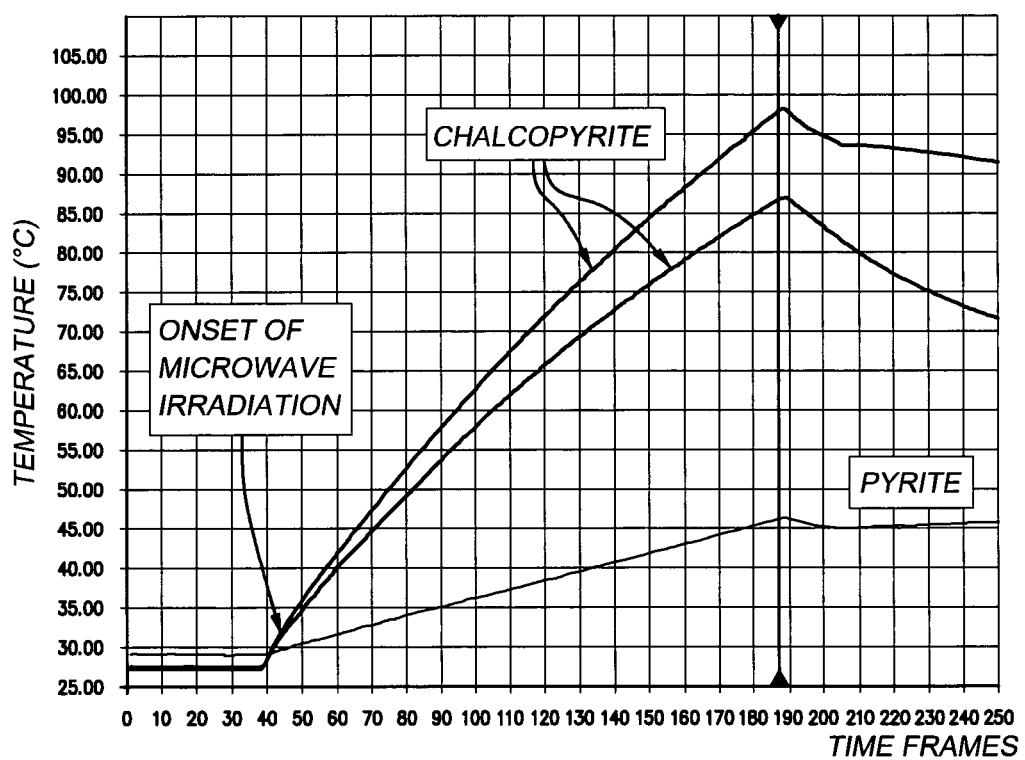
FIG. 10 is a graph showing the change in temperature of the grains in FIG. 9 with time as they are subjected to microwave radiation.

FIG. 9 is an IR image of two chalcopyrite grains (right) and a pyrite grain (left) after exposure to microwave irradiation. The differential heating of mineralized areas within each chalcopyrite grain is immediately clear. In contrast, the pyrite grain undergoes little to no temperature change. Quantification of the heating rate of each grain with time is depicted in FIG. 10. Clearly, the rate of heating and the temperature increase of the chalcopyrite grains are much higher than the pyrite grain.

Figure 11:
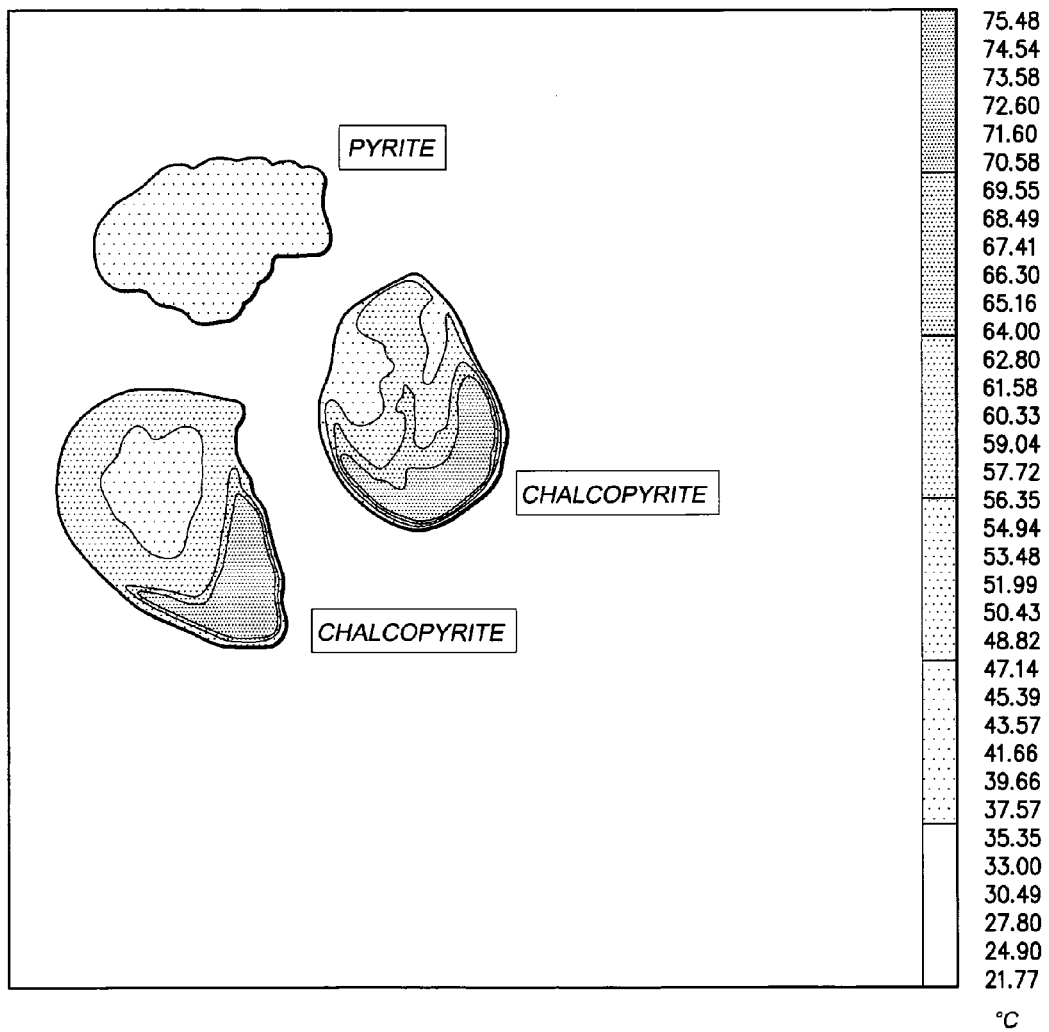
FIG. 11 is yet another IR image of two chalcopyrite grains (bottom and right) and a pyrite grain (top) after exposure to microwave irradiation.
Figure 12:
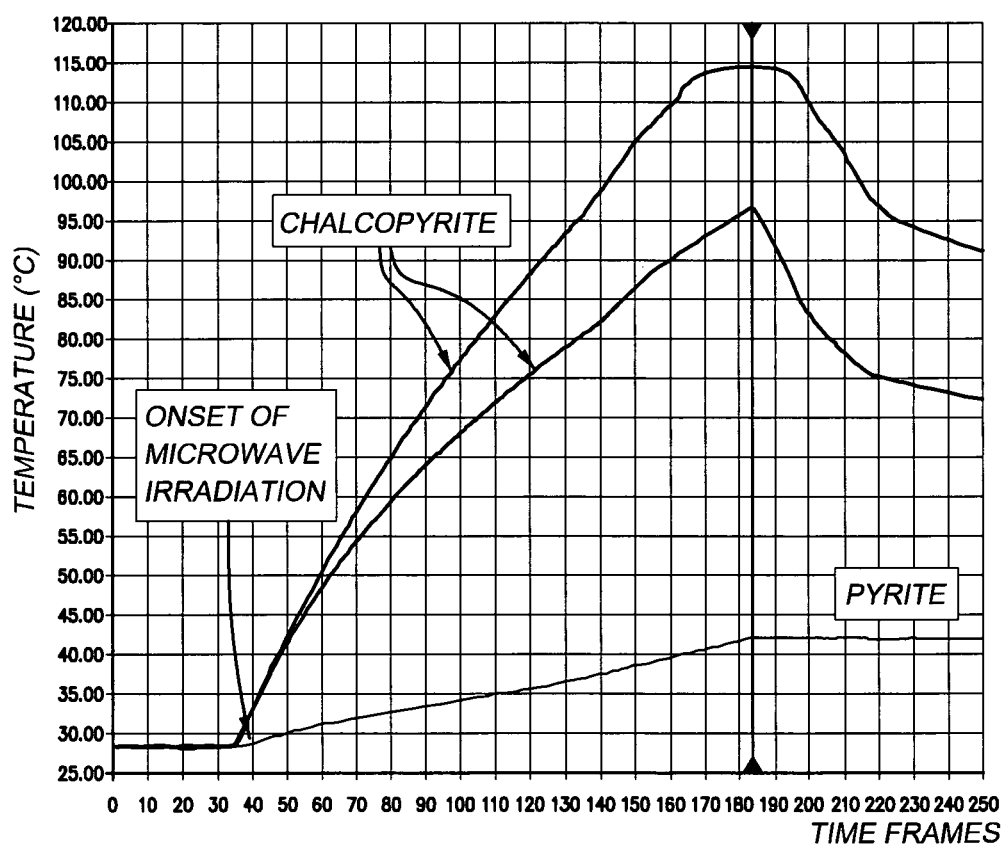
FIG. 12 is a graph illustrating the change in temperature of the grains in FIG. 11 with time as they are subjected to microwave radiation.

FIG. 11 is yet another IR image of two chalcopyrite grains (bottom and right) and a pyrite grain (top) after exposure to microwave irradiation. A graph of the temperature increase with time of the grains in FIG. 11 is illustrated in FIG. 12.

Figure 13:
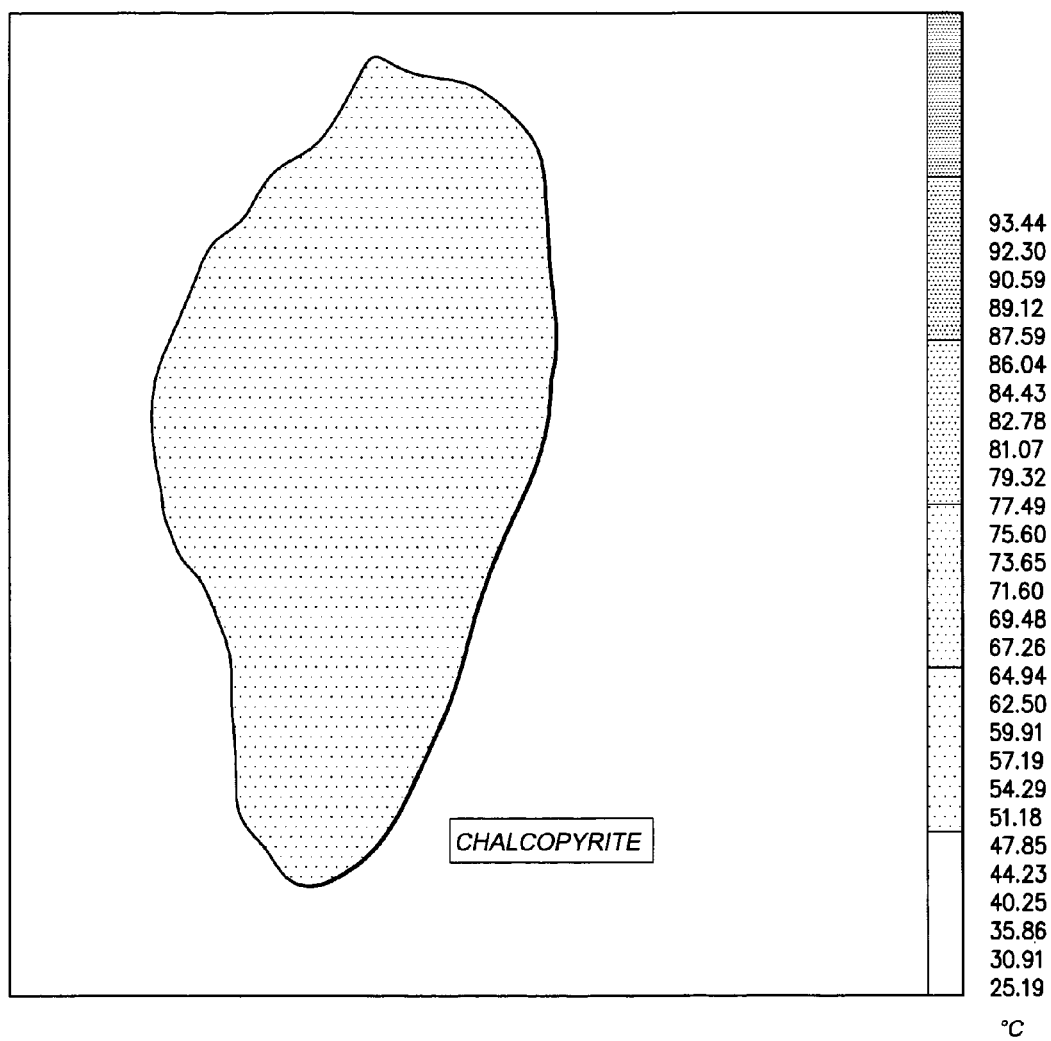
FIG. 13 is an IR image of a chalcopyrite grain prior to application with microwave radiation.
Figure 14:
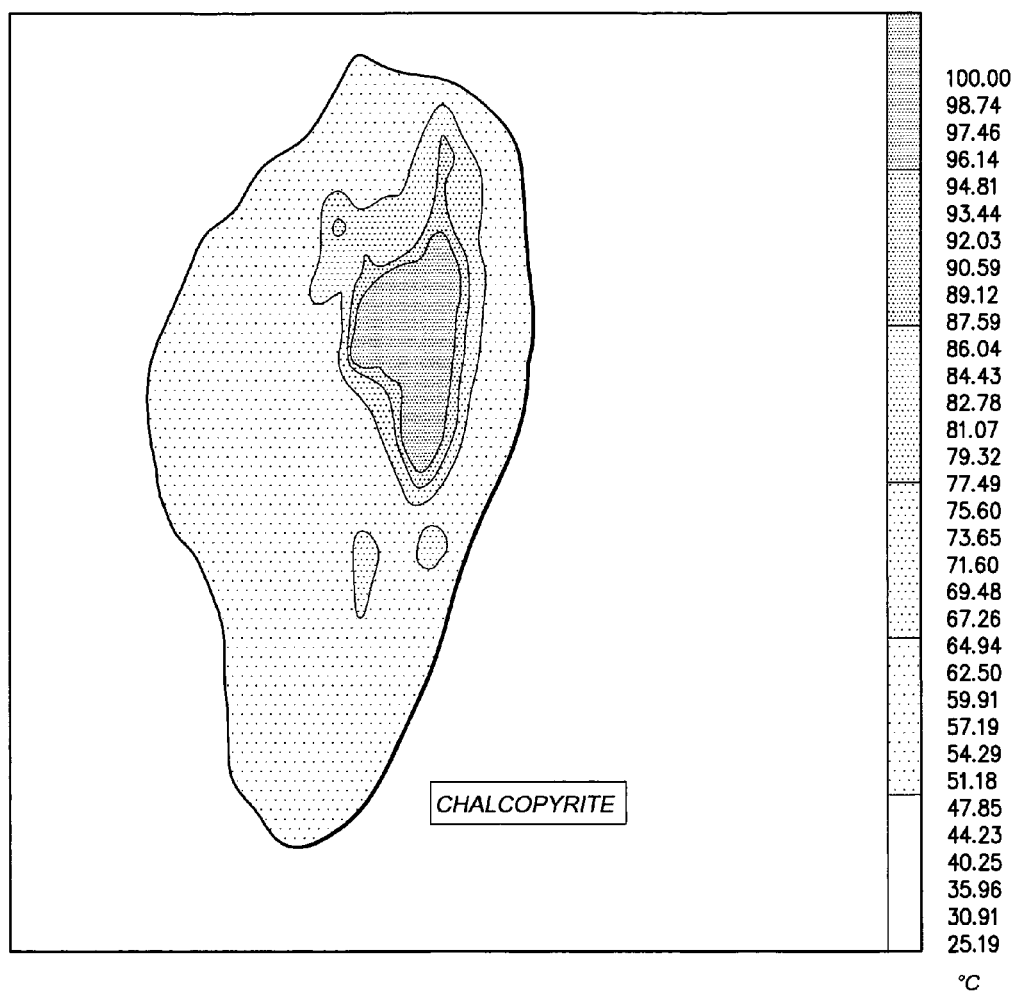
FIG. 14 is an IR image of the chalcopyrite grain in FIG. 13 after one second of exposure to microwave radiation.

FIG. 13 is an IR image of a chalcopyrite grain prior to application with microwave radiation. As expected, the grain exhibits a low and uniform temperature. FIG. 14 is an IR image of the chalcopyrite grain in FIG. 13 after irradiation with microwave radiation for one second. The areas of localised heating on the grain are immediately evident. Advantageously, this allows one to gauge the level and location of mineral content within the grain before the heat dissipates to the relatively cooler regions of the grain and/or the surroundings.

Figure 15:
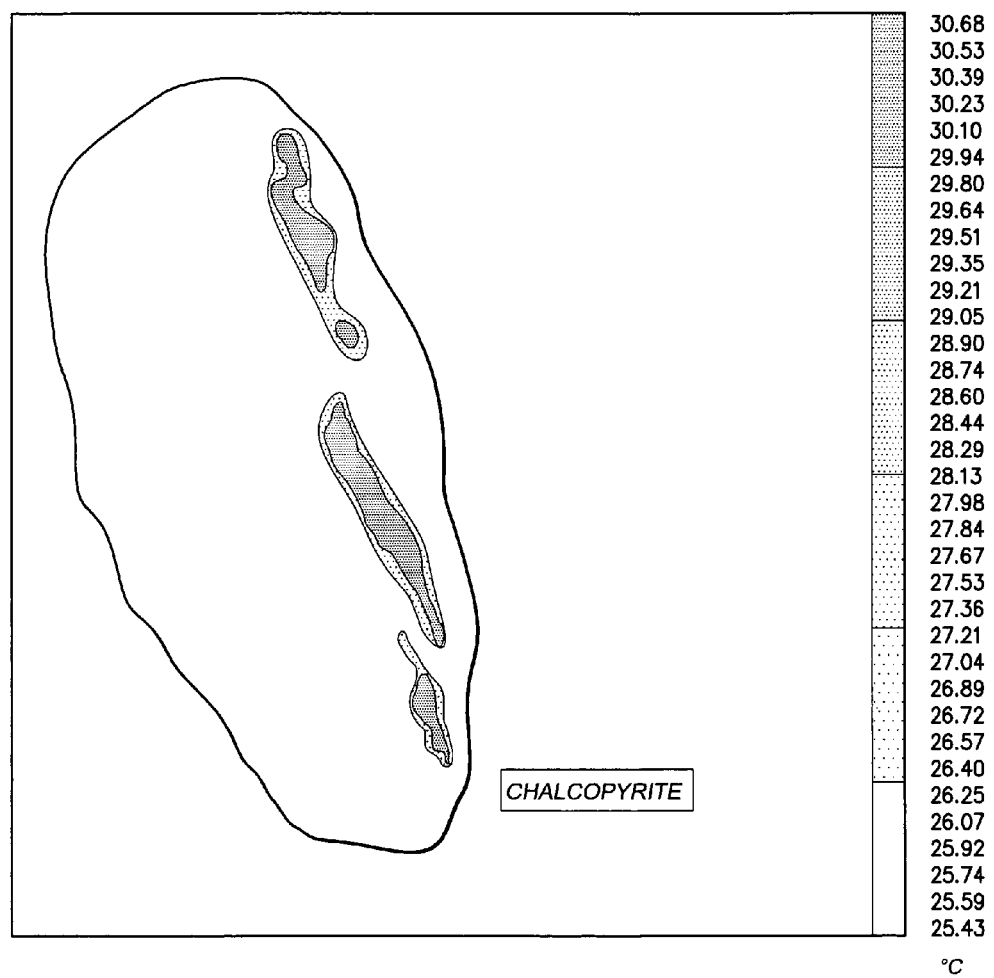
FIG. 15 is an IR image of a quartzite/chalcopyrite grain captured after 0.2 seconds of exposure to pulsed microwave radiation.

FIG. 15 is an IR image of a quartzite/chalcopyrite grain captured after 0.2 seconds of pulsed microwave radiation. The image highlights the heated regions on the grain before dissipation of the heat to other parts of the grain or the surroundings occurs.

Figure 16:
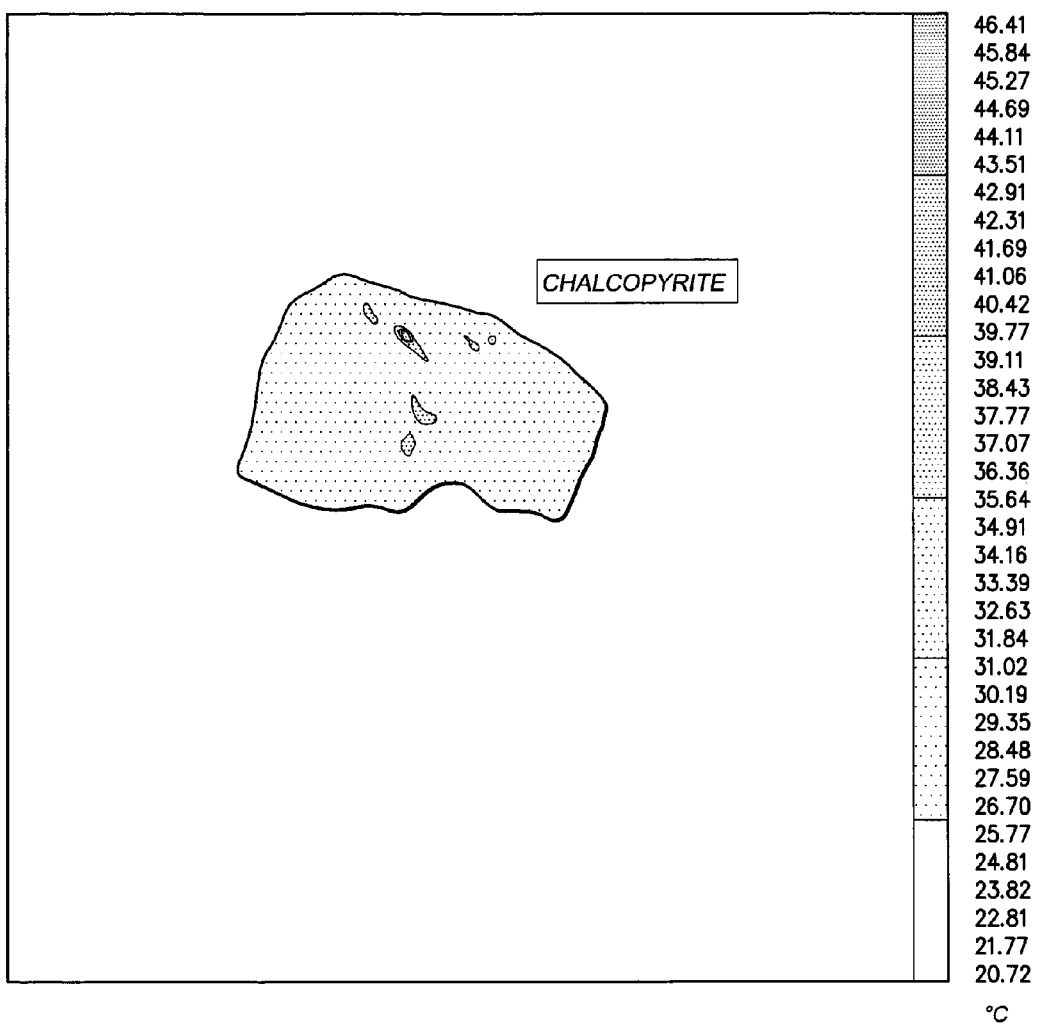
FIG. 16 is another IR image of a quartzite/chalcopyrite grain captured after 0.2 seconds of exposure to pulsed microwave radiation.

FIG. 16 is another IR image of a quartzite/chalcopyrite grain captured after 0.2 seconds of pulsed microwave radiation. In this case, the grain contains relatively little chalcopyrite.

Figure 17:
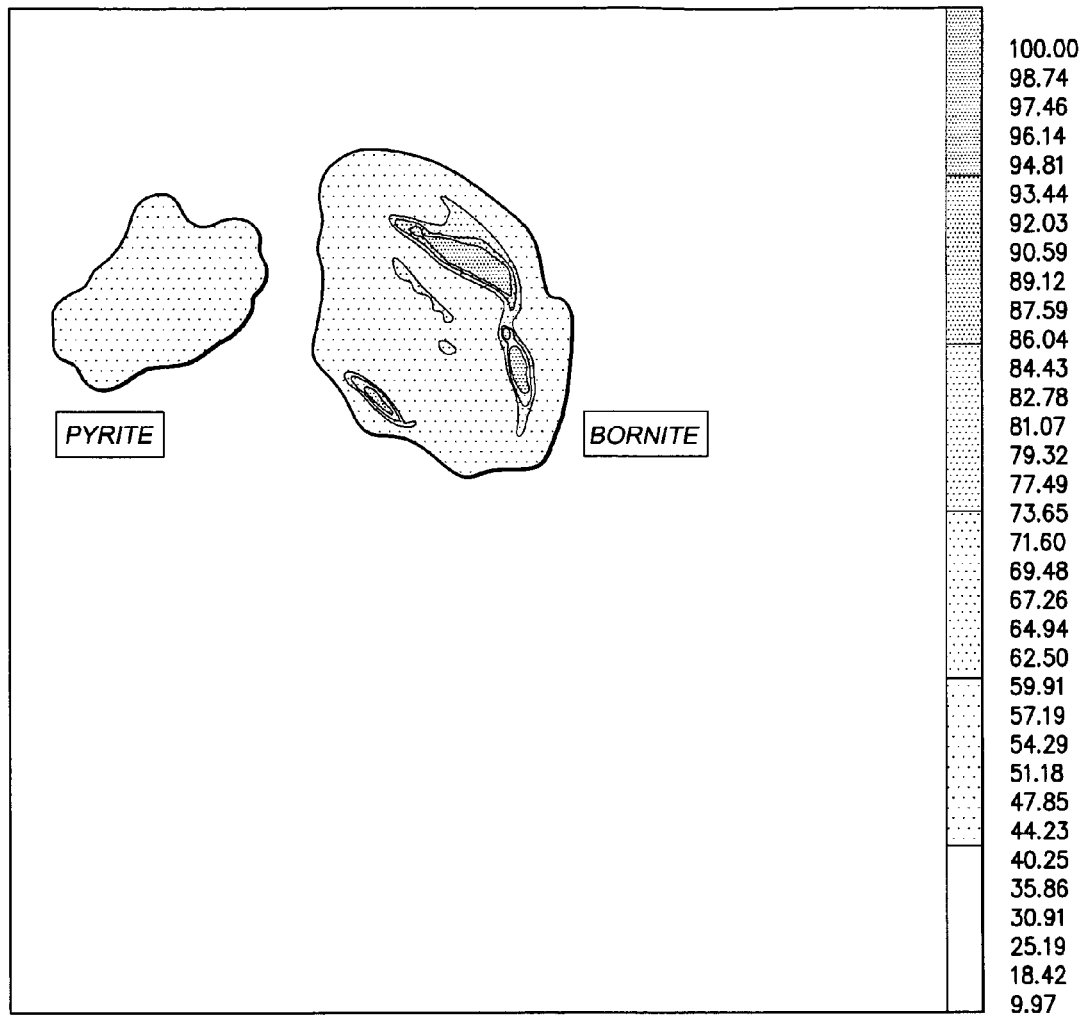
FIG. 17 is an IR image of a pyrite mineral grain (left) and a bornite mineral grain (right) after exposure to microwave radiation.

FIG. 17 is an IR image of a pyrite mineral grain (left) and a bornite mineral grain (right) after exposure to pulsed microwave irradiation with a peak power of 3 kW for 10% of the exposure time in a single mode cavity. The total duration of heating was 5 seconds. The heated regions of the bornite grain are immediately evident whereas the temperature of the pyrite grain has remained relatively low and uniform throughout.

Figure 18:
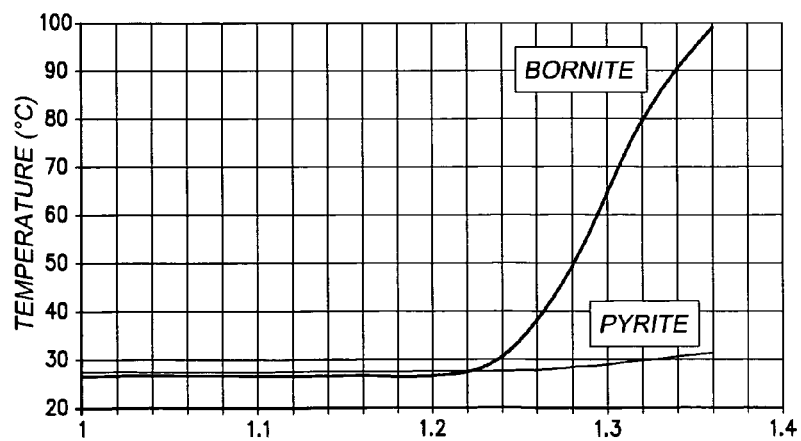
FIG. 18 is a graph showing the change in temperature of the mineral grains in FIG. 17 with time as they are subjected to microwave radiation.

FIG. 18 is a graph showing the change in temperature of the mineral grains in FIG. 17 with time as they are subjected to microwave radiation. As observed in the image of FIG. 17, the rate of heating of the bornite grain is much higher than the pyrite grain. Accordingly, the method is effective for distinguishing between bornite and pyrite samples.

Figure 19:
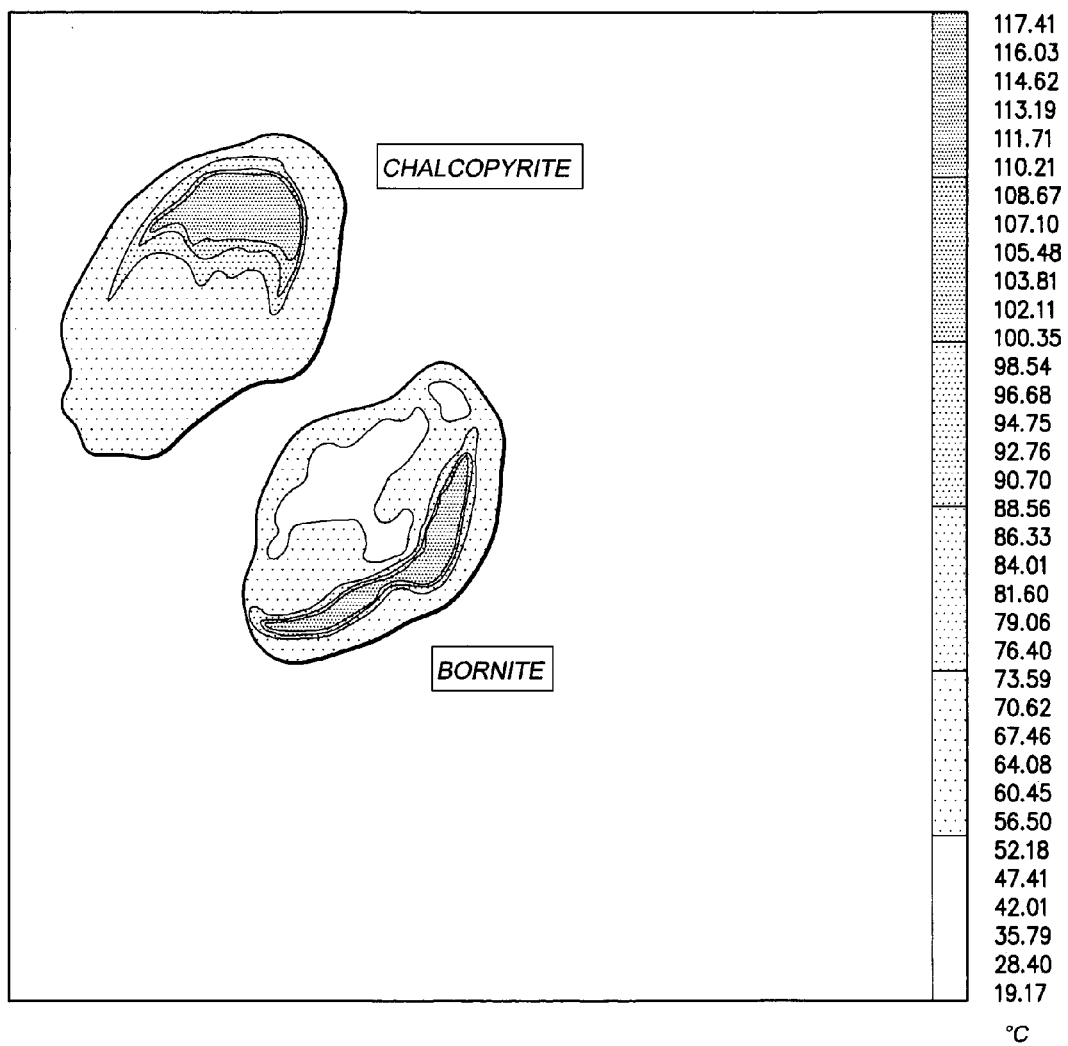
FIG. 19 is an IR image of a chalcopyrite mineral grain (top) and a bornite mineral grain (bottom) after exposure to microwave radiation.
Figure 20:
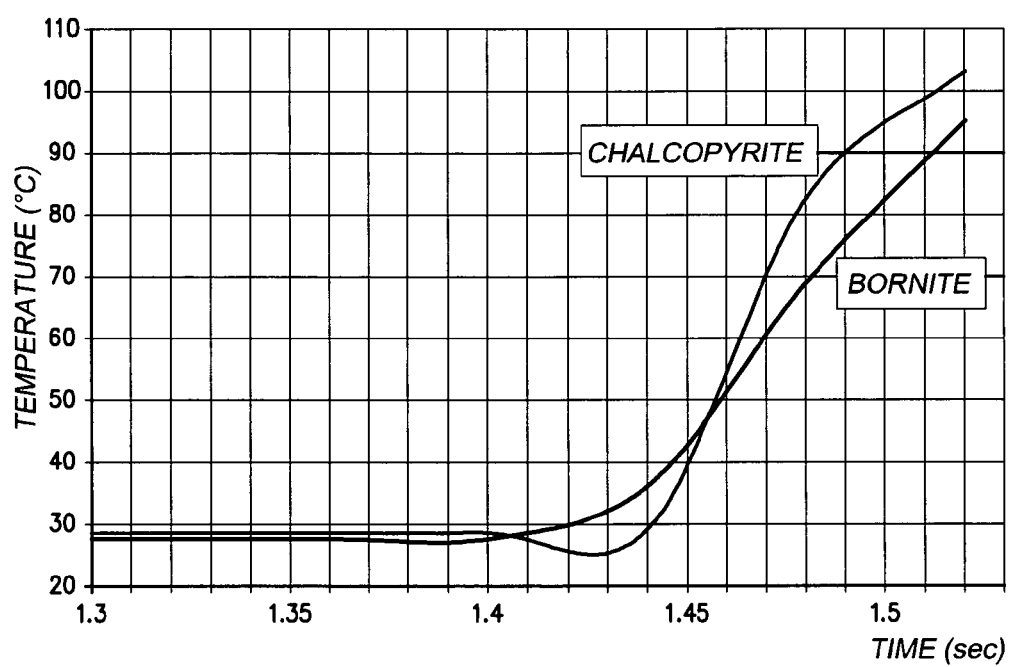
FIG. 20 is a graph showing the change in temperature of the mineral grains in FIG. 19 with time as they are subjected to microwave radiation.

FIG. 19 is an IR image of a chalcopyrite mineral grain (top) and a bornite mineral grain (bottom) after exposure to microwave irradiation. Both grains show significant heating in localised regions of their structure and their rates of heating are similar (FIG. 20).

It will of course be realised that the above has been given only by way of illustrative example of the invention and that all such modifications and variations thereto as would be apparent to persons skilled in the art are deemed to fall within the broad scope and ambit of the invention as herein set forth.

The invention claimed is:

1. A method of detecting a mineral in a target material, the method comprising:
   (a) applying electromagnetic radiation to the material;
   (b) detecting thermal radiation emitted from the material during or immediately after exposure of the material to the electromagnetic radiation;
   (c) determining the rate of heating of the material, or a part thereof; and
   (d) analysing the thermal radiation to determine the presence of the mineral in the material.

2. A method of detecting a mineral in a material, the method comprising:
   (a) applying electromagnetic radiation to the material;
   (b) detecting thermal radiation emitted from the material during or immediately after exposure of the material to the electromagnetic radiation;
   (c) determining a rate of heating of the material, or a part thereof; and
   (d) analysing the rate of heating to determine the presence of the mineral in the material.

3. The method defined in claim 1 wherein the thermal radiation emitted from the material is detected during exposure of the material to the electromagnetic radiation.

4. The method defined in claim 1 wherein the thermal radiation emitted from the material is detected within 2.0 seconds of exposure of the material to the electromagnetic radiation.

5. The method defined in claim 1 wherein the thermal radiation emitted from the material is detected within 1.0 second of exposure of the material to the electromagnetic radiation.

6. The method defined in claim 1 wherein the thermal radiation emitted from the material is detected within 0.5 seconds of exposure of the material to the electromagnetic radiation.

7. The method defined in claim 1 wherein step (a) comprises selecting the electromagnetic radiation and exposure conditions to heat the mineral to a temperature which is significantly higher than a temperature of other components of the material.

8. The method defined in claim 1 wherein the electromagnetic radiation is low energy radiation having an energy density less than 1000 MW/m$^3$.

9. The method defined in claim 1 wherein the electromagnetic radiation is microwave energy.

10. The method defined in claim 1 wherein the electromagnetic radiation is continuous or pulsed.

11. The method defined in claim 10 wherein at least one of a pulse duration and a frequency of the electromagnetic radiation is selected such that:
   (a) heating of at least one of surface moisture and absorbed moisture within the material is minimised;
   (b) a thermal differential between the electromagnetic radiation absorbing mineral and other components in the material is maximized, the other components in the material including gangue material;
   (c) heating of the gangue material is minimised; and
   (d) the mineral in the material is affected by the electromagnetic radiation.

12. The method defined in claim 10 wherein a duration of pulses of the electromagnetic radiation is up to 1 second.

13. The method defined in claim 10 wherein a duration of pulses of the electromagnetic radiation is 0.01 second to 1 second.

14. The method defined in claim 10 wherein in situations where the electromagnetic radiation is microwave radiation, the pulsed microwave radiation is applied at a power density below 1000 MW/m$^3$.

15. The method defined in claim 10 wherein in situations where the electromagnetic radiation is microwave radiation, the pulsed microwave radiation is applied at a power density in a range of 1 MW/m$^3$ to 100 MW/m$^3$.

16. The method defined in claim 10 wherein in situations where the electromagnetic radiation is microwave radiation, a frequency of the radiation is in a range of 400 MHz to 5800 MHz.

17. A method of sorting a feed stream of material into at least two streams, the method including:
   (a) determining the presence of a target mineral in the feed stream of material using the method defined in claim 1; and
   (b) separating the feed stream of material into the at least two streams based on that determination.

18. An apparatus for determining the presence of a target mineral within a material, the apparatus including:
   (a) an electromagnetic radiation exposure zone including an electromagnetic radiation emitter adapted to emit radiation into the exposure zone;
   (b) a detector configured to detect thermal radiation emitted from the material during an application of electromagnetic radiation to the material; and
   (c) an analyser for determining a rate of heating of the material, or portion thereof, based on the thermal radiation detected by the detector, and for thereby determining the presence of the mineral within the material.

19. The apparatus defined in claim 18 wherein the electromagnetic radiation emitter is adapted to emit pulsed radiation into the exposure zone.

20. The apparatus defined in claim 18 wherein the exposure zone is arranged such that the material being analysed passes vertically through the exposure zone.

21. The apparatus defined in claim 18 wherein the detector is a thermal imager.

22. The apparatus defined in claim 21 wherein the thermal imager is located within 50 cm of rock or rock fragments passing through the exposure zone.

23. The method defined in claim 2 wherein the thermal radiation emitted from the material is detected during exposure of the material to the electromagnetic radiation.

24. The method defined in claim 2 wherein the thermal radiation emitted from the material is detected within 2.0 seconds of exposure of the material to the electromagnetic radiation.

25. The method defined in claim 2 wherein the thermal radiation emitted from the material is detected within 1.0 second of exposure of the material to the electromagnetic radiation.

26. The method defined in claim 2 wherein the thermal radiation emitted from the material is detected within 0.5 seconds of exposure of the material to the electromagnetic radiation.

27. The method defined in claim 2 wherein step (a) comprises selecting the electromagnetic radiation and exposure conditions to heat the mineral to a temperature which is significantly higher than a temperature of other components of the material.

28. The method defined in claim 2 wherein the electromagnetic radiation is low energy radiation having an energy density less than 1000 MW/m$^3$.

29. The method defined in claim 2 wherein the electromagnetic radiation is microwave energy.

30. The method defined in claim 2 wherein the electromagnetic radiation is continuous or pulsed.

31. The method defined in claim 30 wherein at least one of a pulse duration and a frequency of the electromagnetic radiation is selected such that:
    (a) heating of at least one of surface moisture and absorbed moisture within the material is minimised;
    (b) a thermal differential between the electromagnetic radiation absorbing mineral and other components in the material is maximized, the other components in the material including gangue material;
    (c) heating of the gangue material is minimised; and
    (d) the mineral in the material is affected by the electromagnetic radiation.

32. The method defined in claim 30 wherein a duration of pulses of the electromagnetic radiation is up to 1 second.

33. The method defined in claim 30 wherein a duration of pulses of the electromagnetic radiation is 0.01 second to 1 second.

34. The method defined in claim 30 wherein in situations where the electromagnetic radiation is microwave radiation, the pulsed microwave radiation is applied at a power density below 1000 MW/m$^3$.

35. The method defined in claim 30 wherein in situations where the electromagnetic radiation is microwave radiation, the pulsed microwave radiation is applied at a power density in a range of 1 MW/m$^3$ to 100 MW/m$^3$.

36. The method defined in claim 30 wherein in situations where the electromagnetic radiation is microwave radiation, a frequency of the radiation is in a range of 400 MHz to 5800 MHz.

37. A method of sorting a feed stream of material into at least two streams, the method including:
    (a) determining the presence of a target mineral in the feed stream of material using the method defined in claim 2; and
    (b) separating the feed stream of material into the at least two streams based on that determination.

* * * * *

UNITED STATES PATENT AND TRADEMARK OFFICE
CERTIFICATE OF CORRECTION

PATENT NO.       : 8,545,094 B2  
APPLICATION NO. : 13/202935  
DATED            : October 1, 2013  
INVENTOR(S)      : Nenad Djordjevic Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 224 days.

Signed and Sealed this

Fifteenth Day of September, 2015

Michelle K. Lee
*Director of the United States Patent and Trademark Office*